(12) United States Patent
Okechukwu et al.

(10) Patent No.: US 9,561,162 B1
(45) Date of Patent: Feb. 7, 2017

(54) COMBINED DENTAL WHITENING, POLISHING, AND RE-MINERALIZING SYSTEM

(71) Applicants: Okey Okechukwu, Irving, TX (US); Xiaofeng Meng, Fort Worth, TX (US)

(72) Inventors: Okey Okechukwu, Irving, TX (US); Xiaofeng Meng, Fort Worth, TX (US)

( * ) Notice: Subject to any disclaimer, the term of this patent is extended or adjusted under 35 U.S.C. 154(b) by 0 days.

(21) Appl. No.: 15/234,181

(22) Filed: Aug. 11, 2016

Related U.S. Application Data

(60) Provisional application No. 62/203,674, filed on Aug. 11, 2015.

(51) Int. Cl.

| | |
|---|---|
| *A61K 8/22* | (2006.01) |
| *A61Q 11/00* | (2006.01) |
| *A61K 8/58* | (2006.01) |
| *A61K 8/21* | (2006.01) |
| *A61K 8/49* | (2006.01) |

(52) U.S. Cl.
CPC . *A61K 8/22* (2013.01); *A61K 8/21* (2013.01); *A61K 8/4953* (2013.01); *A61K 8/585* (2013.01); *A61Q 11/00* (2013.01); *A61K 2800/28* (2013.01); *A61K 2800/592* (2013.01)

(58) Field of Classification Search
USPC .............................. 424/49, 50, 53, 401, 486
See application file for complete search history.

(56) References Cited

U.S. PATENT DOCUMENTS

2009/0175917 A1* 7/2009 Engelbrecht ........... A61Q 11/00
424/401
2013/0189201 A1* 7/2013 Buelo ...................... A61K 8/19
424/53

* cited by examiner

*Primary Examiner* — Walter Webb
(74) *Attorney, Agent, or Firm* — Richard G. Eldredge

(57) ABSTRACT

A combined dental whitening, polishing, and re-mineralizing liquid formula includes an oxidizer; an abrasive; mineral salt; and a catalyst.

4 Claims, 3 Drawing Sheets

COMBINED DENTAL WHITENING, POLISHING, AND RE-MINERALIZING SYSTEM

BACKGROUND

1. Field of the Invention

The present invention relates generally to dental whitening systems, and more specifically, to a combined system for simultaneously bleaching, polishing, and re-mineralizing teeth.

2. Description of Related Art

Dental whitening systems are well known in the art and are effective means to bleach, whiten, or re-mineralize teeth. For example, FIG. 1 depicts a conventional dental whitening system 101 having an aqueous mixture 103 applied to one or more teeth 105, via an applicator 107. Among a variety of other compounds, aqueous mixture 103 generally includes one or more of an oxidizer (e.g., hydrogen peroxide), abrasives (e.g., silicon dioxide), or a mineral salt (e.g., sodium fluoride), not shown. In use, the presence of the oxidizer, abrasive, or mineral respectively serve to bleach, polish, or re-mineralize the teeth 105.

One of the problems commonly associated with system 101 is that aqueous mixture 103 is not stable, limiting use. For example, hydrogen peroxide is very reactive and must therefore be cooled long term to prevent the chemical from breaking down and losing its potency for bleaching teeth. However, cooling aqueous mixture 103 to stabilize the peroxide also slows down the chemical reactions that would result in the desired bleaching effect. This is seen as a disadvantage of conventional dental whitening systems.

Another disadvantage of conventional dental whitening systems is that the compounds necessary to re-mineralize and polish the teeth do not readily dissolve into aqueous mixture 103. For example, calcium fluoride, a relatively benign compound, does not dissolve readily into aqueous mixture 103 so the significantly more toxic sodium fluoride is often used. Alternatively, conventional dental whitening systems forgo the steps of re-mineralization or polishing the teeth 105 such that these steps must be completed separately.

Accordingly, although great strides have been made in the area of dental whitening systems, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
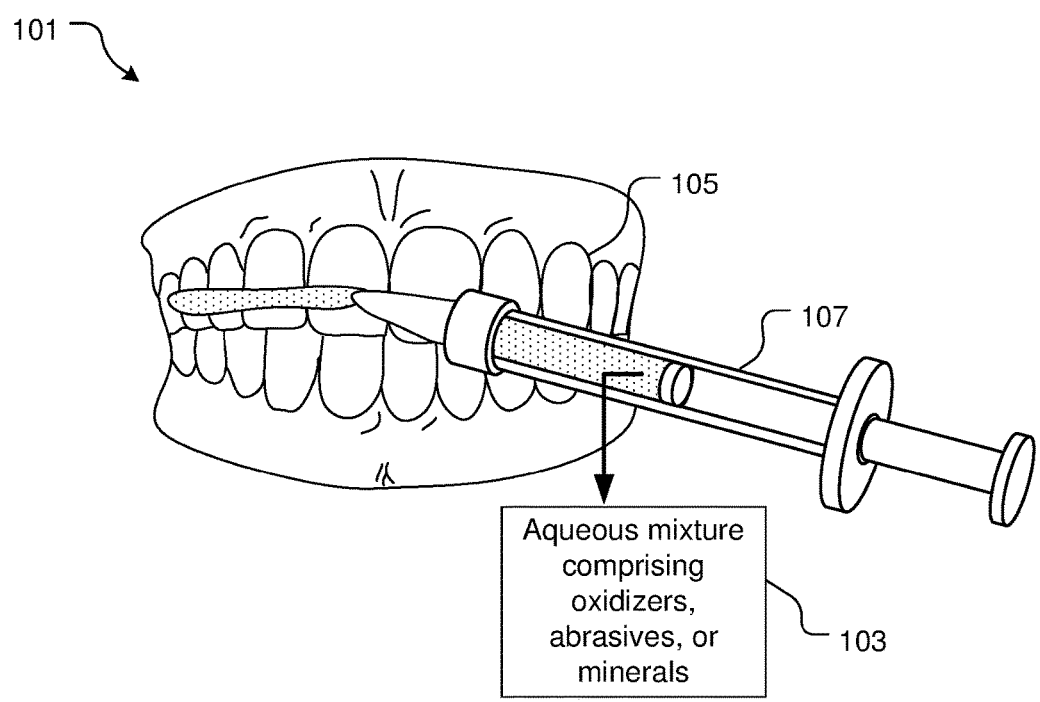
FIG. 1 is a simplified front view of a conventional dental whitening system.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional dental bleaching systems. Specifically, a stabilized aqueous solution allows for reduced storage requirements and increased long-term potency of the solution. In addition, the stabilized aqueous solution can more easily incorporate benign substances for dental re-mineralization. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
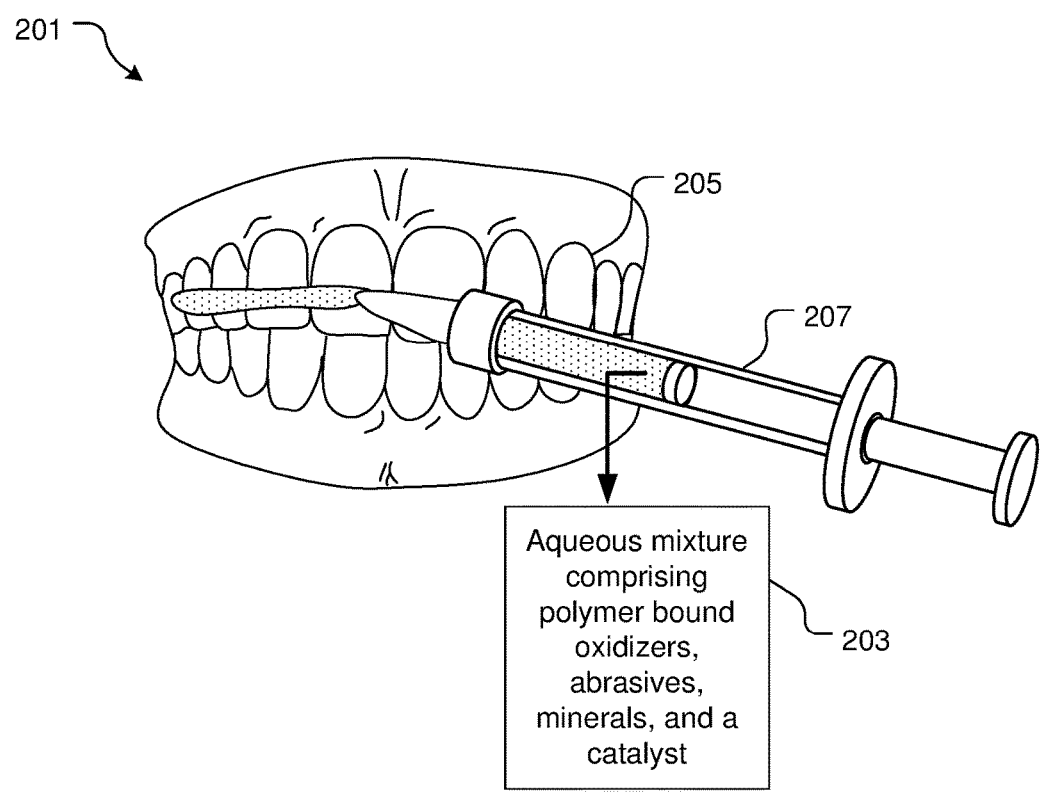
FIG. 2 is a simplified front view of a combined dental whitening, polishing, and re-mineralizing system in accordance with a preferred embodiment of the present application.

Referring now to the drawings wherein like reference characters identify corresponding or similar elements throughout the several views, FIG. 2 depicts a front view of a combined dental whitening, polishing, and re-mineralizing system 201 in accordance with a preferred embodiment of the present application. It will be appreciated that system 201 overcomes one of more of the above-listed problems commonly associated with conventional dental bleaching systems.

In the contemplated embodiment, system 201 comprises an aqueous mixture 203 applied to one or more teeth 205, via an applicator 207. Among a variety of other compounds, aqueous mixture 203 generally includes one or more of an oxidizer (e.g., hydrogen peroxide), abrasives (e.g., silane), mineral salt (e.g., calcium fluoride), and a catalyst (e.g., Flavin), (refer to FIG. 3). In use, the presence of the oxidizer, abrasive, and mineral respectively serve to bleach, polish, and re-mineralize the teeth 205 while the catalyst accelerates these processes.

It should be appreciated that one of the unique features believed characteristic of the present application is that the oxidizer, abrasive, and mineral components of mixture 203 are stabilized within the solution by the presence of one or more polymers, (e.g., polyacylate), allowing the presence of all three effects within a single step of an individual's personal or professional dental treatment.

Figure 3:
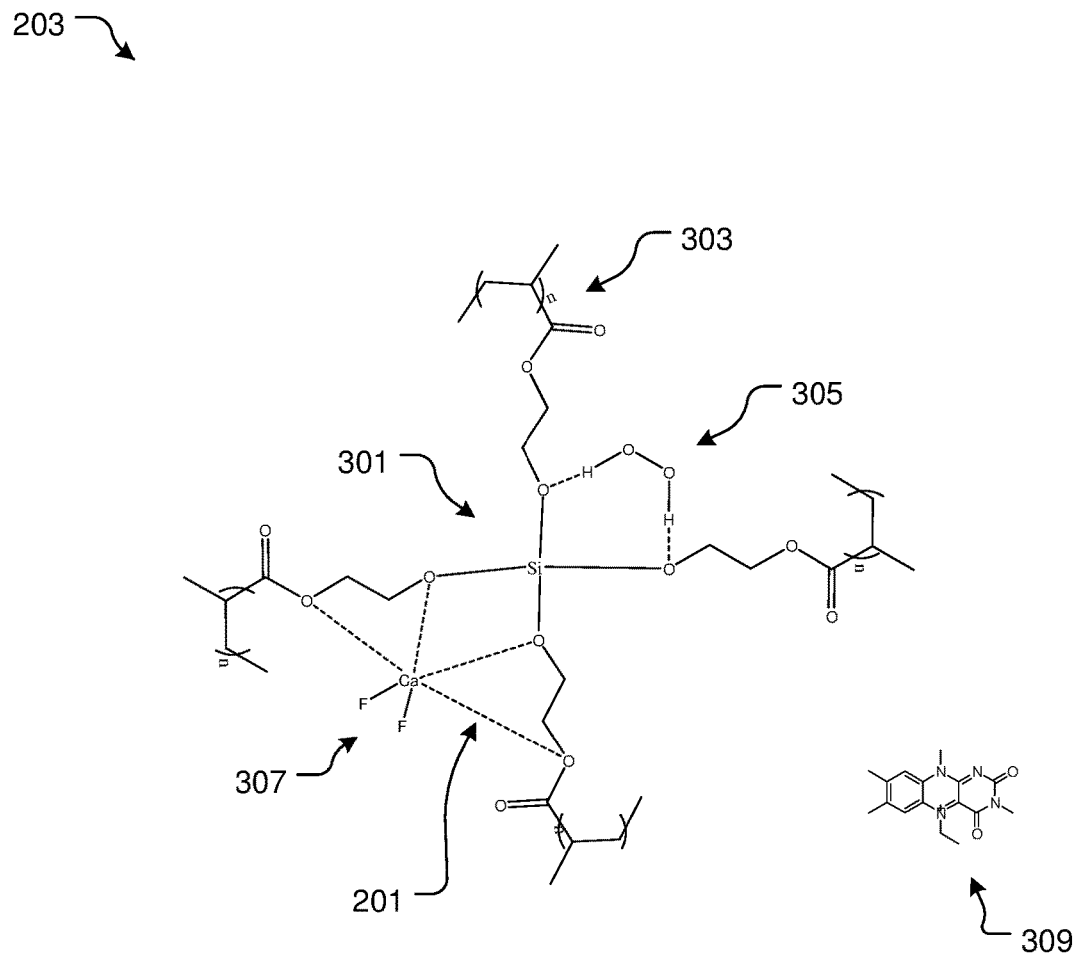
FIG. 3 is a chemical rendering of the aqueous mixture of FIG. 2.

Referring now to FIG. 3 a chemical rendering of the polymer stabilized aqueous mixture 203 of FIG. 2 is shown. In the preferred embodiment a silane compound 301 bonds to 4 polymer chains 303 of sufficient length that they create a binding or chelating site for both the peroxide compound 305 and the re-mineralization compound 307. It is understood and will be appreciated that, bound in this way, all relevant components of aqueous mixture 203 are stable in solution.

It is contemplated and will be appreciated that silane compound 301 not only forms the core of the resulting stabilized superstructure, but also serves as the abrasive component of the mixture 203. Further, although the preferred embodiment shows the use of a silane and polymer to create binding and chelating, it is contemplated that other combined compounds can do so. Specifically, the use of multiple polymers or large sulfurous compounds, e.g., thiourea, in lieu of silane and a polymer, are contemplated herein.

Another unique feature believed characteristic of the present application is that because peroxide 305 is stable in mixture 203, the long term potency of the peroxide increases and the need for reaction slowing storage solutions, such as refrigeration or cooling, decreases.

Another unique feature believed characteristic of the present application is that mineral 307 need not be readily dissolved in mixture 203, increasing the range of useable products to healthier compounds such as calcium fluoride.

The preferred embodiment also contemplates the use of a catalyst 309, e.g., Flavin, to more readily convert the components of mixture 203 from their stable superstructure to their chemical or physical purpose when applied to the teeth (see FIG. 2). It is contemplated and will be appreciated that catalyst 309 can be added to mixture 203 immediately prior to or during use to further maintain the long-term stability of the mixture components.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A combined dental whitening, polishing, and re-mineralizing liquid formula, consisting essentially of:
   an oxidizer;
   an abrasive;
   mineral salt; and
   a catalyst;
   wherein the catalyst is Flavin.

2. The formula of claim 1, wherein the oxidizer is hydrogen peroxide.

3. The formula of claim 1, wherein the abrasive is a silane.

4. The formula of claim 1, wherein the mineral salt is calcium fluoride.

* * * * *